United States Patent [19]

Noda et al.

[11] 4,150,137

[45] Apr. 17, 1979

[54] PYRIDYLALKYL ESTERS OF 2-(P-ISOBUTYLPHENYL)ACETIC ACID AND PROPIONIC ACIDS AND USE

[75] Inventors: Kanji Noda, Chikushino; Akira Nakagawa; Yuji Ishikura, both of Tosu; Hiroyuki Ide, Fukuoka, all of Japan

[73] Assignee: Hisamitsu Pharmaceutical Co. Inc., Tosu, Japan

[21] Appl. No.: 845,237

[22] Filed: Oct. 25, 1977

Related U.S. Application Data

[62] Division of Ser. No. 748,454, Dec. 8, 1976.

[30] Foreign Application Priority Data

Dec. 24, 1975 [JP] Japan ................................ 50-156799

[51] Int. Cl.² ..................... A61K 31/44; C07D 213/55
[52] U.S. Cl. ............... 424/263; 260/326.43; 260/347.4; 424/248.55; 424/250; 424/267; 424/274; 424/285; 424/308; 544/171; 544/399; 546/238; 546/342; 560/105
[58] Field of Search .................... 260/295 R, 295.5 R; 424/263

[56] References Cited

U.S. PATENT DOCUMENTS 3,228,831   1/1966   Nicolson et al. .................... 424/308

OTHER PUBLICATIONS

Nakanishi et al., Chem. Abst., vol. 84, 1975, parag. 105414a.

*Primary Examiner*—Richard Raymond
*Attorney, Agent, or Firm*—Browdy and Neimark

[57] ABSTRACT

The present invention relates to phenylacetic acid ester derivatives of the following general formula:

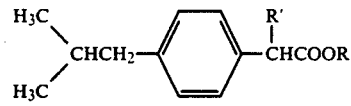

wherein, R is selected from the group consisting of lower alkyl (other than ethyl) and substituted lower alkyl, and R' may be a hydrogen or methyl.

The compounds obtained by the present invention possess a high degree of analgetic ,antipyretic and anti-inflammatory activites and cause little side effects on the gastro-intestinal tracts, when administered orally and topically, and they may be useful as oral and topical analgetics, antipyretics and antiinflammatory agents.

11 Claims, No Drawings

PYRIDYLALKYL ESTERS OF 2-(P-ISOBUTYLPHENYL)ACETIC ACID AND PROPIONIC ACIDS AND USE

This is a division, of application Ser. No. 748,454 filed Dec. 8, 1976 pending.

DETAILED DESCRIPTION

The present invention relates to novel phenylacetic acid ester derivatives of the general formula [A]:

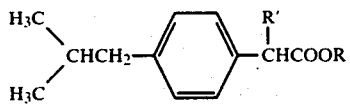

wherein, R is selected from the group consisting of lower alkyl (other than ethyl) and substituted lower alkyl, and R' may be a hydrogen or methyl.

In more details, R in the general formula [A] is explained as follows. R is selected from the group consisting of:

(1) lower alkyl containing up to 6 carbon atoms (other than ethyl), and
(2) the lower alkyl containing up to 6 carbon atoms which is substituted with 1 to 3 substituents such as hydroxyl, halogen, lower alkoxy, lower acyloxy, lower alkoxycarbonyl, hydroxy-lower alkoxy, di-lower alkylamino, cyclic amino, lower cycloalkyl, phenyl, substituted phenyl, tetrahydrofuryl, pyridyl, substituted pyridyl and naphthyl.

In the aforesaid substituted lower alkyl, typical examples of substituents are as follows. Halogen may be chlorine, fluorine, bromine or iodine. Lower alkoxy is methoxy, ethoxy or propoxy. Lower acyloxy is acetoxy or propionyloxy. Lower alkoxycarbonyl is methoxycarbonyl or ethoxycarbonyl. Hydroxylower alkoxy is hydroxyethoxy or hydroxypropoxy. Di-lower alkylamino is dimethylamino or diethylamino. Cyclic amino is morpholino, N-methylpiperazinyl, N-phenylpiperazinyl, N-benzylpiperazinyl, N-(β-hydroxyethyl)piperazinyl, piperidyl or pyrrolidinyl. Lower cycloalkyl is cyclopropyl, cyclobutyl, cyclopentyl or cyclohexyl. Substituted phenyl may be phenyl substituted at any position with 1 or 2 substituents consisting of halogen such as chlorine, fluorine, bromine and iodine, lower alkyl such as methyl, ethyl and isobutyl, lower alkoxy such as methoxy and ethoxy, trifluoromethyl and nitro. Pyridyl is 2-pyridyl, 3-pyridyl or 4-pyridyl. Substituted pyridyl may be pyridyl substituted at any position with halogen such as chlorine, bromine and iodine and methyl.

The compounds of the present invention produce a high degree of analgetic, anti-pyretic and anti-inflammatory activities and little side effects on the gastro-intestinal tracts, when they are administered orally and topically. Therefore, they may be useful as oral and topical analgetics, antipyretics and anti-inflammatory agents.

Adrenalcortical hormone preparations have been used as predominant anti-inflammatory agents for external use. However, even when these preparations are applied topically, their longterm application may often cause untoward side effects. Thus, the non-steroidal anti-inflammatory agents with low toxicity have been demanded for a long time. For this reason, it is said that development of the compounds of the present invention meet fully these demands.

The compounds of the present invention may be represented by the following general formula [A-1] and [A-2]:

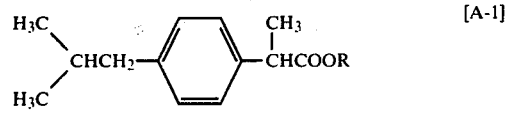

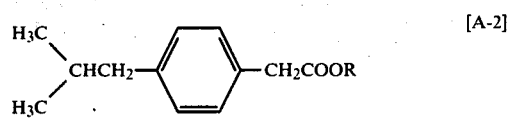

wherein, R has the same meanings as defined above.

In more details, R may be methyl, n-propyl, isopropyl, n-butyl, isobutyl, n-hexyl, hydroxyethyl, dihydroxypropyl, fluoroethyl, bromoethyl, trifluoroethyl, methoxymethyl, ethoxymethyl, methoxyethyl, ethoxyethyl, acetoxymethyl, acetoxyethyl, ethoxycarbonylmethyl, hydroxyethoxyethyl, dimethylaminoethyl, diethylaminoethyl, dimethylaminopropyl, morpholinoethyl, N-methylpiperadinoethyl, cyclopropylmethyl, benzyl, chlorobenzyl, di-chlorobenzyl, fluorobenzyl, trifluoromethylbenzyl, methylbenzyl, methoxybenzyl, phenethyl, fluorophenethyl, methylphenethyl, tetrahydrofurfuryl, pyridylmethyl, pyridylethyl, chloropyridylmethyl or naphthylethyl.

The processes for preparing the compounds of the present invention may be explained in the following. The compounds of the present invention may be obtained in high yields by any one of the following processes [I] to [VIII].

Process [I]:

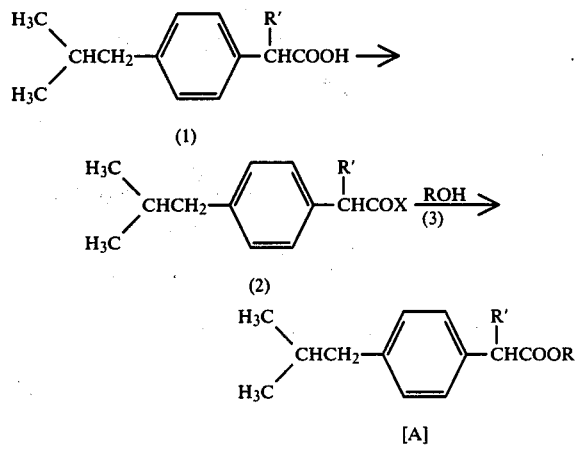

wherein, R and R' have the same meanings as defined above; X may be halogen.

Process [II]:

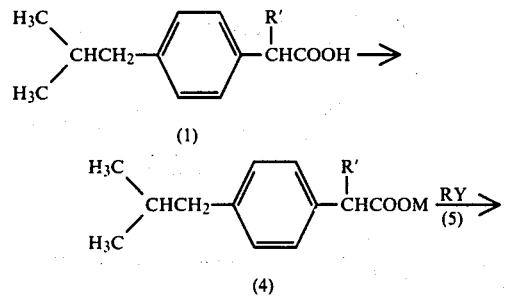

-continued

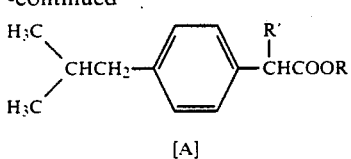
[A]

wherein, R and R' have the same meanings as defined above; M may be alkali metal; Y is selected from halogen and organic sulfonyloxy.

Process [III]:

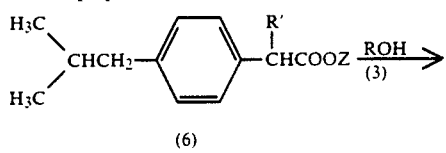

(6)

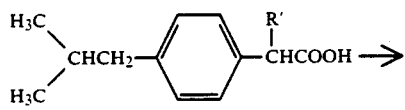
[A]

wherein, R and R' have the same meanings as defined above; Z may be lower alkyl.

Process [IV]:

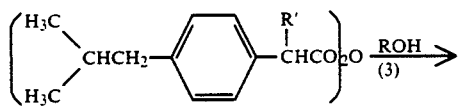
(1)

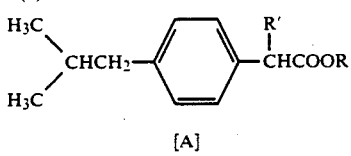
(7)

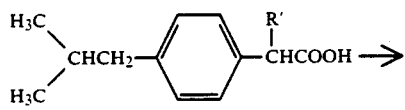
[A]

wherein, R and R' have the same meanings as defined above.

Process [V]:

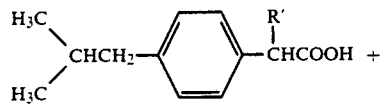
(1)

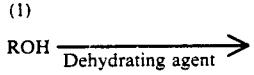
(3)

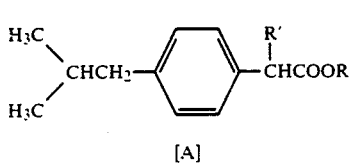
[A]

wherein, R and R' have the same meanings as defined above.'

Process [VI]:

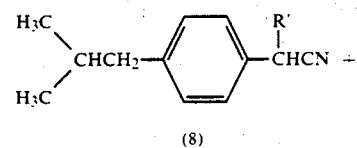
(8)

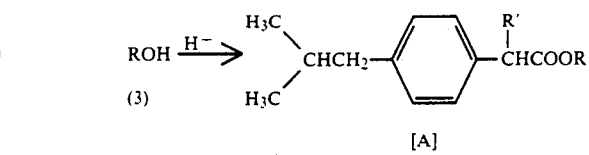
(3)
[A]

wherein, R and R' have the same meanings as defined above.

Process [VII]:

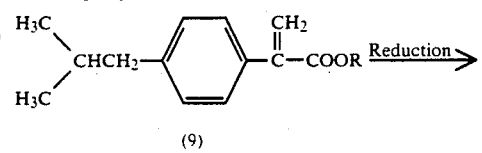
(9)

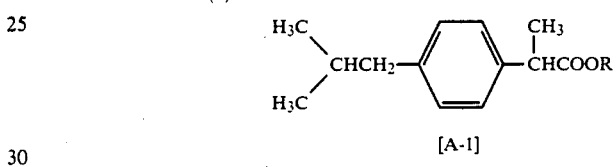
[A-1]

wherein, R has the same meanings as defined above.

Process [VIII]:

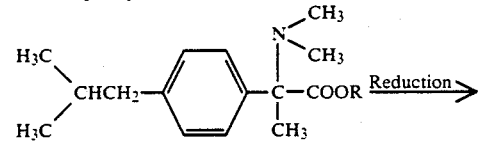
(10)

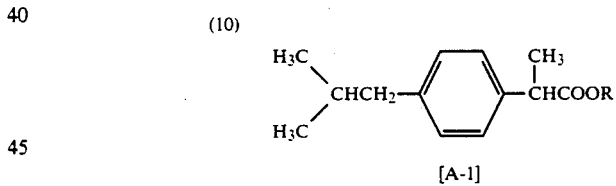
[A-1]

wherein, R has the same meanings as defined above.

Further details of the processes shown by the aforesaid reaction schemes are given in the following.

In the process [I], the p-isobutylphenylacetic acid derivatives of the general formula (1) is treated with a halogenizing agent to produce its acid halide of the general formula (2). Subsequently, the acid halide is allowed to react with the alcohol of the general formula (3) in an unreactive organic solvent such as tetrahydrofuran, diglyme, dioxane, acetone, chloroform, benzene or toluene in the presence of a dehydrating agent such as pyridine, trimethylamine, triethylamine, potassium carbonate or sodium carbonate.

In the process [II], the compound of the general formula (1) is treated with alkali metal to produce the compound of the general formula (4), which is then allowed to react with the alkali halide of the general formula (5) in an organic solvent such as benzene, toluene, xylene, tetrahydrofuran, diglyme, dioxane, dimethylformamide or dimethylsulfoxide. The reaction proceeds smoothly even at room temperature, but promoted by application of heating.

In the process [III], to the compound of the general formula (6) is added the alcohol of the general formula (3) in the large excess which may serve for a reaction solvent. The resulting mixture is heated at or in the vicinity of the boiling point of the alcohol used either with or without adding a small amount of alkali metal to bring about ester interchange. For this reaction, benzene, toluene and xylene may also be used as another preferable solvents.

In the process [IV], the compound of the general formula (7) is allowed to heat with the alcohol of the general formula (3) in excess either with or without adding an acid catalyst. Another organic solvents which do not participate in the reaction may also be used for this reaction.

In the process [V], the compound of the general formula (1) is reacted with the alcohol of the general formula (3) under reflux in the presence of a dehydrating agent such as sulfuric acid poly-phosphoric acid or p-toluenesulfonic acid. Such organic solvents as benzene, toluene and xylene are used as preferable reaction solvents. The use of large excess of the alcohols [III] may also serve for reaction solvents.

In the process [VI], a nitrile of the general formula (8) is heated with the alcohol of the general formula (3) in the presence of an acid catalyst, for example, sulfuric acid to produce ester derivatives.

In the process [VII] and [VIII], the respective compounds of the general formula (9) and (10) are allowed to reduce in the presence of a catalyst such as palladium carbon or platinum dioxide.

Compound:

All of the compounds of the present invention may be prepared by the aforesaid processes [I]–[VIII], and their examples are shown in Table I including their appearance, boiling points and mass spectra(parent ion).

Table I

Examples of the compounds of the general formula [A] obtained by the present invention

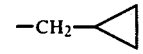

| Compound No. | R' | R | Appearance (Boiling point: °C./mmHg) | Mass spectra (Parent ion) |
|---|---|---|---|---|
| 1 | $CH_3$ | $-CH_3$ | Oil (90°–92°/0.5) | 220 |
| 2 | " | $-CH_2CH_2CH_3$ | " (100°–103°/0.3) | 248 |
| 3 | " | $-CH(CH_3)_2$ | " (91°–92°/0.5) | 248 |
| 4 | " | $-CH_2CH_2CH_2CH_3$ | " (97°–98°/0.1) | 262 |
| 5 | " | $-CH_2CH(CH_3)_2$ | " (84°–87°/0.1) | 262 |
| 6 | " | $-(CH_2)_5CH_3$ | " (131°–133°/0.6) | 290 |
| 7 | " | $-CH_2CH_2F$ | " (110°–111°/1.0) | 238 |
| 8 | " | $-CH_2CH_2Br$ | " (118°–120°/0.1) | 298 |
| 9 | " | $-CH_2CF_3$ | " (73°–74°/0.12) | 288 |
| 10 | " | $-CH_2CH_2OH$ | " (138°–139°/1.0) | 250 |
| 11 | " | $-CH_2CH(OH)CH_2OH$ | " (153°–154°/1.0) | 280 |
| 12 | " | $-CH_2OCH_3$ | " (75°–76°/1.0) | 250 |
| 13 | " | $-CH_2OC_2H_5$ | " (118°–119°/1.0) | 264 |
| 14 | " | $-CH_2CH_2OCH_3$ | " (108°–110°/0.7) | 264 |
| 15 | " | $-CH_2CH_2OC_2H_5$ | " (126°–127°/1.0) | 278 |
| 16 | " | $-CH_2CH_2OCH_2CH_2OH$ | " (140°–142°/0.15) | 294 |
| 17 | " | $-CH_2OCOCH_3$ | " | 278 |
| 18 | " | $-CH_2CH_2OCOCH_3$ | " (120°–122°/0.1) | 292 |
| 19 | " | $-CH_2COOC_2H_5$ | " (123°–124°/0.23) | 292 |
| 20 | " | $-CH_2-\triangleleft$ (cyclopropyl) | " (109°–111°/1.0) | 260 |
| 21 | " | 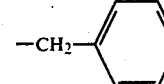 | " (108°–110°/0.1) | 296 |
| 22 | " | 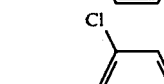 | " (145°–147°/0.5) | 330 |
| 23 | " | 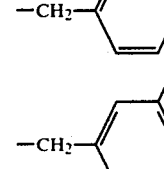 | " (148°–149°/0.18) | 330 |

Table I-continued

Examples of the compounds of the general formula [A] obtained by the present invention $$\text{(H}_3\text{C)}_2\text{CHCH}_2-\text{C}_6\text{H}_4-\text{CH(R')COOR} \quad [A]$$

| Compound No. | R' | R | Appearance (Boiling point: °C./mmHg) | Mass spectra (Parent ion) |
|---|---|---|---|---|
| 24 | " | —CH$_2$—C$_6$H$_4$—Cl (p) | " (153°–155°/0.5) | 330 |
| 25 | " | —CH$_2$—C$_6$H$_4$—F (o) | " (136°–137°/0.2) | 314 |
| 26 | " | —CH$_2$—C$_6$H$_4$—F (m) | " (143°–144°/0.2) | 314 |
| 27 | " | —CH$_2$—C$_6$H$_4$—F (p) | " (118°–120°/0.2) | 314 |
| 28 | " | —CH$_2$—C$_6$H$_4$—CF$_3$ (p) | " (142°–145°/0.8) | 364 |
| 29 | " | —CH$_2$—C$_6$H$_4$—CH$_3$ (o) | " (145°–148°/0.28) | 310 |
| 30 | " | —CH$_2$—C$_6$H$_4$—CH$_3$ (m) | " (119°–121°/0.2) | 310 |
| 31 | " | —CH$_2$—C$_6$H$_4$—CH$_3$ (p) | " (139°–140°/0.1) | 310 |
| 32 | " | —CH$_2$—C$_6$H$_4$—OCH$_3$ (p) | " (149°–151°/0.1) | 326 |
| 33 | " | —CH$_2$—C$_6$H$_3$—(Cl)$_2$ (2,3) | " (153°–155°/0.1) | 364 |
| 34 | " | —CH$_2$CH$_2$—C$_6$H$_5$ | " (142°–144°/0.18) | 310 |
| 35 | " | —CH$_2$CH$_2$—C$_6$H$_4$—F (m) | " | 328 |

Table I-continued

Examples of the compounds of the general formula [A] obtained by the present invention $$(CH_3)_2CHCH_2-\text{C}_6\text{H}_4-CHR'COOR \quad [A]$$

| Compound No. | R' | R | Appearance (Boiling point: °C./mmHg) | Mass spectra (Parent ion) |
|---|---|---|---|---|
| 36 | " | —CH₂CH₂—C₆H₄—F | " | 328 |
| 37 | " | —CH₂CH₂—C₆H₄—CH₃ | (155°–160°/0.2) | 324 |
| 38 | " | —CH₂CH(CH₃)—C₆H₄—CH₂CH(CH₃)₂ | (162°–165°/0.2) | 380 |
| 39 | " | —CH₂CH₂N(CH₃)₂ | (133°–136°/1.0) | 277 |
| 40 | " | —CH₂CH₂N(C₂H₅)₂ | (129°–130°/1.0) | 305 |
| 41 | " | —CH₂CH₂CH₂N(CH₃)₂ | (115°–117°/1.0) | 291 |
| 42 | " | —CH₂CH₂—N(morpholino) | (128°–131°/1.0) | 319 |
| 43 | " | —CH₂CH₂—N(4-methylpiperazino) | (130°–135°/1.0) | 332 |
| 44 | " | —CH₂-(2-pyridyl) | (138°–140°/0.15) | 297 |
| 45 | " | —CH₂-(3-pyridyl) | (138°–139°/1.0) | 297 |
| 46 | " | —CH₂-(4-pyridyl) | (140°–142°/0.18) | 297 |
| 47 | " | —CH₂-(2-chloro-3-pyridyl) | (142°–145°/0.1) | 331 |
| 48 | " | —CH₂CH₂-(2-pyridyl) | (114°–115°/0.3) | 311 |
| 49 | " | —CH₂-(tetrahydrofuran-2-yl) | (109°–110°/1.0) | 290 |
| 50 | " | —CH₂CH₂-(2-naphthyl) | colorless needles 52°–54° C.* | 360 |

Table I-continued

Examples of the compounds of the general formula [A] obtained by the present invention $$\underset{H_3C}{\overset{H_3C}{>}}CHCH_2-\underset{}{\bigcirc}-\underset{CHCOOR}{\overset{R'}{|}} \quad [A]$$

| Compound No. | R' | R | Appearance (Boiling point; °C./mmHg) | Mass spectra (Parent ion) |
|---|---|---|---|---|
| 51 | H | —$CH_2CF_3$ | Oil (78°–79°/1.0) | 274 |
| 52 | " | —$CH_2CH_2OH$ | " (115°–117°/1.0) | 236 |
| 53 | " | —$CH_2CHCH_2OH$<br>    $\|$<br>    $OH$ | " | 266 |
| 54 | " | —$CH_2OCH_3$ | " (90°–91°/0.15) | 236 |
| 55 | " | —$CH_2OC_2H_5$ | " (116°–118°/1.0) | 250 |
| 56 | " | —$CH_2CH_2OCH_3$ | " (97°–98°/1.0) | 250 |
| 57 | " | —$CH_2CH_2OC_2H_5$ | " (108°–110°/1.0) | 264 |
| 58 | " | —$CH_2CH_2OCOCH_3$ | " (126°–128°/1.0) | 278 |
| 59 | " | —$CH_2$—phenyl | " (124°–126°/1.0) | 282 |
| 60 | " | —$CH_2$—(2-Cl-phenyl) | " (145°–147°/1.0) | 316 |
| 61 | " | —$CH_2$—(4-Cl-phenyl) | " (140°–142°/1.0) | 316 |
| 62 | " | —$CH_2$—(2-F-phenyl) | " | 300 |
| 63 | " | —$CH_2$—(3-F-phenyl) | " | 300 |
| 64 | " | —$CH_2$—(4-$CH_3$-phenyl) | " | 296 |
| 65 | " | —$CH_2$—(4-$OCH_3$-phenyl) | " | 312 |
| 66 | " | —$CH_2$—(2,6-di-Cl-phenyl) | " (90°–91°/1.0) | 350 |
| 67 | " | —$CH_2CH_2$—N$(CH_3)_2$ | " (110°–111°/1.0) | 263 |
| 68 | " | —$CH_2CH_2$—N$(C_2H_5)_2$ | " (115°–117°/1.0) | 291 |
| 69 | " | —$CH_2CH_2CH_2$—N$(CH_3)_2$ | " (110°–111°/1.0) | 277 |

Table I-continued

Examples of the compounds of the general formula [A] obtained by the present invention

[A structural formula is shown: H3C-CH(CH3)-CH2-[phenyl ring with R']-CH(COOR)]

| Compound No. | R' | R | Appearance (Boiling point: °C./mmHg) | Mass spectra (Parent ion) |
|---|---|---|---|---|
| 70 | " | —CH₂CH₂—N(morpholine ring with O) | (109°–110°/1.0) | 305 |
| 71 | " | —CH₂CH₂—N(piperazine ring)—N—CH₃ | " | 318 |
| 72 | " | —CH₂—(pyridine, N at 2-position) | (103°–104°/1.0) | 283 |
| 73 | " | —CH₂—(pyridine, N at 3-position) | (142°–145°/1.0) | 283 |
| 74 | " | —CH₂—(pyridine, N at 4-position) | (106°–108°/1.0) | 283 |
| 75 | " | —CH₂—(chloropyridine, Cl at 2-position) | (150°–153°/1.0) | 317 |
| 76 | " | —CH₂—(tetrahydrofuran, O) | (73°–75°/0.15) | 276 |

*Only this value represents the melting point.

All of the compounds of the present invention were first tested for their acute toxicities, and subsequently for their pharmacological activities such as anti-inflammatory and analgetic activity. It is found that certain of the compounds of the present invention have shown a high degree of pharmacological activities with low toxicity. Especially, topical application of the said compounds have produced a higher anti-inflammatory potency than that of ibuprofen. The testing methods are described in the following, and the results are summarized in Table II.

(1) Acute toxicity

Each test compound suspended in 0.5% tragacanth-saline was administered intraperitoneally or orally to male mice of dd-strain(body weight 16–24 g). The lethal dose was estimated from the death of animals 72 hours following administration.

(2) Anti-inflammatory activity for oral route

A group of five male rats of Wistar-strain(body weight 100–150 g) were orally given each test compound suspended in 0.5% tragacanth-saline. After 30 minutes 0.5–1.0% carrageenin suspended in the water for injection was injected subcutaneously to a hind paw. After 3 hours the carrageenin edema was measured by volume, and the percent inhibition was determined with respect to the results for the control animals. For comparison, the percent inhibition of each test compound of the present invention was divided by that of the reference compound, ibuprofen [2-(p-isobutylphenyl)propionic acid] to give the relative inhibition, which is included in Table II. The mean percent inhibition of ibuprofen was 37.4% at a dose of 50 mg/kg and 33.5% at 10 mg/kg.

(3) Anti-inflammatory activity for topical route

The dorsal skin of male rats of Wistar-strain(body weight: about 100 g) were depilated. Carrageenin suspension was injected intra-dermally at a dose of 250 γ/0.05 ml/site. The filter paper (size: 2.3 cm in diameter) was impregnated with 1% test compound dissolved in polyethylene glycol 300. Immediately after injection, the filter paper containing 125.2±18.0 mg of the polyethylene glycol was applied on the injected site. After 3 hours, 1% pontamine sky blue solution was injected intravenously at a dose of 0.5 ml/kg. After further 3 hours, the animals were sacrificed and their dorsal skin were removed to measure the area of leakage of the pigment. The percent inhibition was determined with respect to the results for the control animals. For comparison, the percent inhibition of each test compound of the present invention was divided by that of the reference compound, ibuprofen, to give the relative inhibition. The mean percent inhibition of ibuprofen was 23.8%.

(4) Analgetic activity

Each test compound suspended in 0.5% tragacanth-saline was orally administered to dd-strain mice(body weight: 18–20 g). After one hour 0.6% acetic acid solution was injected intraperitoneally in a volume of 0.1 ml/10 g. The writhing syndrome was observed for 10 minutes from 30 minutes after injection, and 50% analgetic effective dose($ED_{50}$) and its 95% confidence limit were calculated by Litchfield-Wilcoxon's method.

Table II

Pharmacological Effects and Acute Toxicity of the Object Compound, Phenylacetic Acid Derivatives obtained by the Present Invention:

| Standard compound | anti-inflammatory effect oral 50 mg/kg | 10 mg/kg | topical | analgetic effect $ED_{50}$ (mg/kg) (95%C.L.) | acute toxicity (mg/kg) oral |
|---|---|---|---|---|---|
| ibuprofen | 1.0 | 1.0 | 1.0 | 45.8 (42.1–49.5) | 1000–2000 |

Object Compound of General Formula [A]

| R' | R | 50 mg/kg | 10 mg/kg | topical | $ED_{50}$ (mg/kg) (95%C.L.) | acute toxicity (mg/kg) oral |
|---|---|---|---|---|---|---|
| $CH_3$ | $-CH_3$ | 1.4 | 0.8 | 3.5 | 109.2 (107.3–111.1) | >2000 |
| " | $-CH_2CH_2CH_3$ | 1.1 | 0.7 | 3.2 | 192.3 (158.3–226.3) | >2000 |
| " | $-(CH_2)_5CH_3$ | 1.2 | — | 3.5 | 214.9 (197.9–231.9) | >2000 |
| " | $-CH_2CF_3$ | 1.3 | 0.8 | 3.6 | 134.6 (129.4–139.8) | 1000–2000 |
| " | $-CH_2CH_2OH$ | 1.0 | 0.5 | 1.9 | 154.9 (148.8–161.0) | >2000 |
| " | $-CH_2CHCH_2OH$ \| OH | 0.9 | 1.1 | — | 142.9 (133.4–152.4) | 1000–2000 |
| " | $-CH_2OCH_3$ | 1.2 | 1.0 | 2.5 | 174.2 (145.1–203.3) | 500–1000 |
| " | $-CH_2OC_2H_5$ | 1.0 | 1.3 | 2.8 | 154.9 (151.8–158.0) | >2000 |
| " | $-CH_2CH_2OCH_3$ | 1.2 | 0.4 | 1.2 | 405.5 (396.4–414.6) | 1000–2000 |
| " | $-CH_2CH_2OC_2H_5$ | 0.9 | 0.7 | 1.2 | 155.6 (130.0–181.2) | >2000 |
| " | $-CH_2CH_2OCH_2CH_2OH$ | 0.9 | — | 2.3 | 151.0 (143.3–158.7) | >2000 |
| " | $-CH_2OCOCH_3$ | 0.9 | 0.9 | — | — | — |
| " | $-CH_2CH_2OCOCH_3$ | 1.1 | 0.7 | 2.2 | 307.6 (285.9–329.3) | >2000 |
| " | $-CH_2COOC_2H_5$ | 0.7 | 0.5 | 1.9 | 180.3 (146.3–214.3) | >2000 |
| " |  | 1.6 | 0.8 | 3.7 | 103.3 (98.6–108.0) | 2000 |
| " |  | 0.9 | 0.7 | 3.1 | 118.3 (114.3–122.3) | >2000 |
| " |  | 1.0 | 0.5 | 2.5 | 51.4 (37.1–65.7) | >2000 |
| " |  | 1.0 | 0.5 | 2.8 | 486.4 (477.9–494.9) | >2000 |
| " |  | 1.7 | 1.6 | 2.9 | 201.9 (183.2–220.6) | — |

Table II-continued
Pharmacological Effects and Acute Toxicity of the Object Compound, Phenylacetic Acid Derivatives obtained by the Present Invention:
| | | | | | | |
|---|---|---|---|---|---|---|
| " | 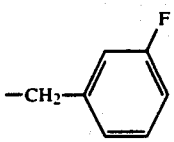 | 1.7 | 0.8 | 0.9 | 633.9 (619.7–648.1) | — |
| " | 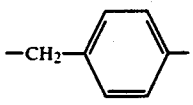 | 1.2 | 1.1 | — | — | — |
| " | 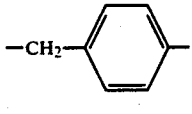 | 1.5 | 1.7 | 1.9 | 229.6 (190.1–269.2) | — |
| " | 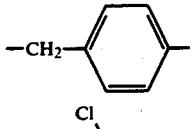 | 1.4 | 0.8 | 2.3 | 219.8 (203.2–236.4) | — |
| " | 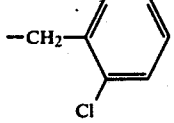 | 1.0 | 0.6 | 2.1 | 79.6 (70.9–88.3) | >2000 |
| " |  | 1.2 | 0.8 | 2.0 | 53.7 (15.0–92.4) | 1000–2000 |
| " |  | 0.9 | 1.2 | 3.0 | 317.7 (304.4–331.0) | 500–1000 |
| " |  | 1.1 | 0.7 | 2.2 | 29.9 (24.7–35.1) | 500–1000 |
| " | 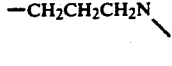 | 0.9 | 0.7 | 1.6 | 154.2 (149.3–159.1) | 1000–2000 |
| " | 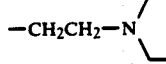 | 1.1 | 1.0 | 2.5 | 31.6 (19.8–43.4) | 1000–2000 |
| " | 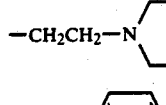 | 1.8 | 0.7 | 4.0 | 67.8 (32.5–103.1) | 1000–2000 |
| " | 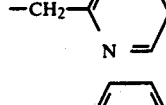 | 1.4 | 1.0 | 1.7 | 31.2 (26.2–36.2) | 1000–2000 |
| " | 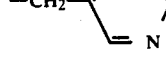 | 1.2 | 1.0 | 2.7 | 87.1 (81.2–93.0) | >2000 |
| " | 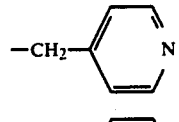 | 2.5 | 0.8 | 1.8 | 762.0 (755.9–768.1) | >2000 |

Table II-continued
Pharmacological Effects and Acute Toxicity of the Object Compound, Phenylacetic Acid Derivatives obtained by the Present Invention:

| | | 0.9 | 0.6 | 3.1 | 91.6 (56.0-127.2) | 1000-2000 |
|---|---|---|---|---|---|---|
| 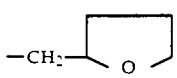 | | | | | | |

Some of the preferred embodiments of the present invenion are disclosed in the following examples.

EXAMPLE 1

A mixture of 3.3 g of 2-(p-isobutylphenyl)propionic acid sodium salt, 2.3 g of dimethylaminoethyl chloride and 30 ml of benzene was refluxed for 12 hours. A solid mass produced was filtered off, and the benzene was distilled away from the filtrate under reduced pressure to leave an oily residue. This redidue was distilled under reduced pressure to give 3.5 g of 2-(p-isobutylphenyl)-propionic acid dimethylaminoethyl ester as a colorless oil, boiling at 133°-136° C./1 mmHg. Analysis-Calculated for $C_{17}H_{27}NO_2$: C, 73.61; H, 9.81; N, 5.05. Found: C, 73.50; H, 9.72; N, 5.02. The infrared spectrum showed strong C=O absorption at 1730 cm$^{-1}$ characteristic for ester. Mass spectrum: parent ion 277 m/e.

EXAMPLE 2

A mixture of 0.05 g of sodium and 8 ml of 3-hydroxymethylpyridine was heated at 65°-70° C. for 10 hours. To this mixture was added 3.8 g of 2-(p-isobutylphenyl)-propionic acid methyl ester, and the whole was heated at 95°-100° C. for 8 hours. After cooling to room temperature, 100 ml of water was added. The resulting mixture was extracted with ether, and the ether was distilled away from the extract to leave a residue. The residue was passed through a column of silica gel, and the adsorbate was eluted with chloroform. The eluates were freed of chloroform in vacuo to give 2.9 g of 2-(p-isobutylphenyl)propionic acid-3-pyridylmethyl ester as a colorless oil. The infrared spectrum showed strong C=O absorption at 1730 cm$^{-1}$ characteristic for ester. Mass spectrum: parent ion 297 m/e.

EXAMPLE 3

To a mixture of 2.28 g of 2-(p-isobutylphenyl)propionic acid sodium salt in 20 ml of dimethylformamide was added 2.52 g of benzyl chloride and the whole was heated at 90° C. for 3 hours. After the reaction was complete, the solvent was removed by distillation under reduced pressure to leave a residue, to which was added water. The resulting mixture was extracted with ether and the extract was dehydrated. The ether was removed by distillation to give an oily product. Distillation of this product under reduced pressure yielded 2.57 g of 2-(p-isobutylphenyl)propionic acid benzyl ester as a colorless oil, boiling at 108°-110° C./0.1 mmHg. Analysis-Calculated for $C_{20}H_{24}O_2$: C, 81.04; H, 8.16. Found: C, 80.92; H, 8.02.

EXAMPLE 4

To a mixture of 2.24 g of 2-(p-isobutylphenyl)propionic acid chloride and 2.10 g of p-methoxybenzyl alcohol in 20 ml of tetrahydrofuran was added 1.50 g of triethylamine under cooling and the whole was stirred for 2 hours. After the reaction was complete, an insoluble matter produced was removed by filtration. The solvent was removed from the filtrate by distillation under reduced pressure. To the residue thus obtained was added water and the resulting mixture was extracted with ether. The ether layer separated was washed with successive, 5% sodium carbonate solution, 5% hydrochloric acid solution and water, and then dehydrated. The ether was removed by distillation to give an oily product. Distillation of this product under reduced pressure yielded 2.81 g of 2-(p-isobutylphenyl)-propionic acid-p-methoxybenzyl ester as a colorless oil, boiling at 149°-151° C./0.1 mmHg. Analysis-Calculated for $C_{21}H_{26}O_3$: C, 77.27; H, 8.03. Found: C, 77.11; H, 8.12.

EXAMPLE 5

A mixture of 4.12 g of 2-(p-isobutylphenyl)propionic acid, 15 ml of 2,2,2-trifluoroethyl alcohol and 4.9 g of concentrated sulfuric acid was heated at 100° C. for 12 hours. After the reaction was complete, the mixture was poured into ice-water and the resulting mixture was extracted with ether. The ether layer separated was washed sufficiently with successive 5% sodium carbonate solution and water, and dehydrated. The ether was removed by distillation to give an oily product. Distillation of the product in vacuo yielded 4.95 g of 2-(p-isobutylphenyl)propionic acid-2,2,2-trifluoroethyl ester as a pale yellow oil, boiling at 73°-74° C./0.12 mmHg. Analysis-Calculated for $C_{15}H_{19}F_3O_2$: C, 62.48; H, 6.64. Found: C, 62.31; H, 6.61.

EXAMPLE 6

A mixture of 0.05 g of sodium in 20 ml of cyclopropylmethyl alcohol was heated at 50° C. for 5 hours. To the mixture was added 2.2 g of 2-(p-isobutylphenyl)propionic acid methyl ester and the whole was refluxed for 10 hours. After the reaction was completed, the solvent was removed by distillation under reduced pressure to leave a residue, to which was added water. The resulting mixture was extracted with ether, and the extract was washed sufficiently with water and then dehydrated. The ether was removed by distillation to leave a residual oily product. This product was then distilled under reduced pressure to yield 1.38 g of 2-(p-isobutylphenyl)propionic acid cyclopropylmethyl ester as a colorless oil, boiling at 109°-111° C./1 mmHg. Analysis-Calculated for $C_{17}H_{24}O_2$: C, 78.42; H, 9.29. Found: C, 78.19; H, 9.22.

EXAMPLE 7

A mixture of 3.0 g of 2-(p-isobutylphenyl)propionic acid anhydride, 3.8 g of 2,2,2-trifluoroethyl alcohol and 0.5 cc of concentrated sulfuric acid was refluxed for 15 hours. After the reaction was complete, the solvent was distilled away under reduced pressure to leave a residue, to which was added water. The resulting mixture was extracted with ether. The ether extract was dehydrated and freed of ether by distillation to give an oily residue. Distillation of the residue under reduced pressure afforded 3.5 g of 2-(p-isobutylphenyl)propionic acid-2,2,2-trifluoroethyl ester as a colorless oil. Mass spectrum:parent ion 288 m/e.

EXAMPLE 8

To a mixture of 2.86 g of 2-(p-isobutylphenyl)acrylic acid-2,2,2-trifluoroethyl ester in 50 ml of methanol was added 0.25 g of palladium-carbon(10%). Hydrogenation was carried out at ordinary temperature and pressure and stopped when a theoretical amount of hydrogen was absorbed. The palladium-carbon was filtered off to give a filtrate. The filtrate was then concentrated in vacuo to yield 2.48 g of 2-(p-isobutylphenyl)propionic acid-2,2,2-trifluoroethyl ester. Mass spectrum: parent ion 288 m/e.

EXAMPLE 9

To a mixture of 0.80 g of 2-dimethylamino-2-(p-isobutylphenyl)propionic acid-2,2,2-trifluoroethyl ester in 20 ml of methanol was added 0.22 g of palladium-carbon(10%). Hydrogenation was carried out at 50°–60° C. for 5 hours. After the reaction was complete, the catalyst was removed by filtration and the filtrate produced was freed of solvent by distillation to give an oily product. This product was distilled in vacuo to give 0.55 g of 2-(p-isobutylphenyl)propionic acid-2,2,2-trifluoroethyl ester as a colorless oil. Mass spectrum: parent ion 288 m/e.

EXAMPLE 10

To a solution of 2.2 g of 2-pyridinemethanol in 20 ml of tetrahydrofuran were added 3 g of 2-(4-isobutylphenyl)propionic acid chloride and subsequently 2.7 g of triethylamine, and the mixture was reacted at room temperature for 2 hours. After the reaction was complete, the crystals produced were removed by filtration. The filtrate was freed of solvent by distillation to leave a residue, to which was added water. The resulting mixture was extracted with ether. The ether extract was dehydrated and freed of ether by distillation. The oily residue thus obtained was distilled in vacuo to give 3.5 g of 2-(4-isobutylphenyl)propionic acid-2-pyridylmethyl ester as a pale yellow oil, boiling at 138°–140° C./0.15 mmHg. Mass spectrum: parent ion 297 m/e.

EXAMPLE 11

To a solution of 5.4 g of 2-(4-isobutylphenyl)propionic acid chloride and 3.7 g of m-fluorobenzyl alcohol in 30 ml of tetrahydrofuran was added 3.7 g of triethylamine, dropwise under cooling, and the mixture was reacted at room temperature for 1.5 hours. After the reaction was complete, the crystals procuced were removed by filtration. The filtrate was freed of solvent by distillation to leave a residue, to which was added water. The resulting mixture was extracted with ether. The ether extract was dehydrated and freed of ether by distillation. The oily residue thus obtained was distilled in vacuo to yield 5.9 g of 2-(4-isobutylphenyl)propionic acid-m-fluorobenzyl ester as a colorless oil, boiling at 143°–144° C./0.2 mmHg. Mass spectrum: parent ion 314 m/e.

EXAMPLE 12

To a solution of 5.4 g of 2-(4-isobutylphenyl)propionic acid chloride and 3.5 g of p-methylbenzyl alcohol in 30 ml of tetrahydrofuran was added 3.7 g of trimethylamine, dropwise under cooling, and reacted at room temperature for 2 hours. After the reaction was complete, the crystals produced were removed by filtration. The filtrate was freed of solvent by distillation to leave a residue, to which was added water. The resulting mixture was extracted with ether, and the extract was dehydrated and freed of solvent by distillation to give an oily residue. This residue was then distilled in vacuo to yield 6.3 g of 2-(4-isobutylphenyl)propionic acid-p-methylbenzyl ester as a colorless oil, boiling at 139°–140° C./0.1 mmHg. Mass spectrum: parent ion 310 m/e.

EXAMPLE 13

A mixture of 5 g of 2-(4-isobutylphenyl)propionic acid, 7.3 g of n-propyl alcohol and 7.1 g of sulfuric acid was refluxed for 6 hours. After cooling, to the mixture was added ice-water. The resulting mixture was extracted with ether, and the extract was dehydrated. The ether was removed by distillation from the extract to leave an oily product. This product was distilled in vacuo to give 5.4 g of 2-(4-isobutylphenyl)propionic acid-n-propyl ester as a colorless oil, boiling at 100°–102° C./0.3 mmHg. Mass spectrum: parent ion 248 m/e.

EXAMPLE 14

To a solution of 3.5 g of p-isobutylphenylacetic acid sodium salt in 20 ml of dimethylformamide was added 5.9 g of o-chlorobenzyl chloride, and the mixture was heated under reflux for 5 hours. After the reaction was complete, the mixture was cooled to produce an inorganic substance, which was then removed by filtration. The filtrate was freed of dimethylformamide by distillation in vacuo to give an oily product. Distillation of this product in vacuo yielded 3.8 g of p-isobutylphenylacetic acid-2-chlorobenzyl ester as a colorless oil, boiling at 145°–147° C/1 mmHg. Analysis-Calculated for $C_{19}H_{21}ClO_2$: C, 72.03; H, 6.68. Found: C, 71.98; H, 6.51. Mass spectrum: parent ion 316 m/e.

EXAMPLE 15

To a solution of 3.5 g of p-isobutylphenylacetic acid chloride in 5.9 g of 2-methoxyethanol was added 1.6 g of triethylamine, and the mixture was stirred at room temperature for 4 hours. After the reaction was complete, an inorganic substance produced was filtered off. The filtrate was extracted with ether, and the extract was washed, dehydrated and applied over a column of silica gel. The adsorbates was eluted with ether, and the eluates were freed of ether to give an oily product. Distillation of the product in vacuo gave 2.8 g of p-isobutylphenylacetic acid-2-methoxyethyl ester as a colorless oil, boiling at 97°–98° C./1 mmHg. Analysis-Calculated for $C_{15}H_{22}O_3$: C, 71.97; H, 8.86. Found: C, 71.63; H, 8.90. Mass spectrum: parent ion 250 m/e.

EXAMPLE 16

A mixture of 1.73 g of 4-isobutylphenylacetonitrile and 10 g of 95% of 2,2,2-trifluoroethanol and 10 g of concentrated sulfuric acid were refluxed for 12 hours. After the reaction was complete, ice-water was added to the mixture. The resulting mixture was extracted with ether. The ether layer separated was dehydrated and concentrated to leave an oily residue. The residue was distilled in vacuo to give 1.4 g of 4-isobutylphenylacetic acid-2,2,2-trifluoroethyl ester as a pale yellow oil, boiling at 77°–79° C./1 mmHg. Analysis-Calculated for $C_{14}H_{17}F_3O_2$: C, 61.30; H, 6.25. Found: C, 61.21; H, 6.23.

EXAMPLE 17

A mixture of 0.05 g of sodium and 8 ml of 3-hydroxymethylpyridine was heated at 65°–70° C. for 10 hours. To this mixture was added 2.1 g of p-isobutylphenylacetic acid methyl ester, and the whole was heated at 95°–100° C. for 8 hours. After the reaction was complete, 100 ml of water was added. The resulting mixture was extracted with ether, and the ether layer separated was dehydrated and concentrated to leave an oily residue. This residue was distilled under reduced pressure to give 1.9 g of p-isobutylphenylacetic acid-3-pyridylmethyl ester as a colorless liquid, boiling at 142°–145° C./1 mmHg. Analysis-Calculated for $C_{18}H_{21}NO_2$: C, 76.29; H, 7.47; N, 4.94. Found: C, 76.02; H, 7.38; N, 4.79. Mass spectrum: parent ion 283 m/e.

EXAMPLE 18

A mixture of 1.9 g of p-isobutylphenylacetic acid, 10 ml of 2,2,2-trifluoroethanol and 1 ml of concentrated sulfuric acid was refluxed for 5 hours. After the reaction was complete, the mixture was poured into ice-water. The resulting mixture was neutralized with adding 5% sodium carbonate solution, and then extracted with ether. The ether layer separated was dehydrated and concentrated to leave an oily residue. The residue was distilled in vacuo to yield 2.3 g of p-isobutylphenylacetic acid-2,2,2-trifluoroethyl ester as a colorless liquid, boiling at 78°–79° C./1 mmHg. Analysis-Calculated for $C_{14}H_{17}F_3O_2$: C, 61.30; H, 6.25. Found: C, 61.01; H, 6.15. Mass spectrum: parent ion 274 m/e.

What is claimed is:

1. A compound of the following formula:

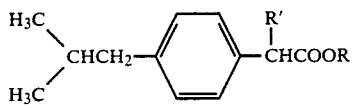

wherein, R is selected from the group consisting of lower alkyl containing up to 6 carbon atoms substituted with 1 to 3 substituents comprising pyridyl or pyridyl substituted at any position with chlorine, bromine, iodine or methyl; and R' is selected from the group consisting of a hydrogen and methyl.

2. A compound in accordance with claim 1 of the following formula:

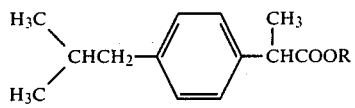

wherein, R is selected from the group consisting of lower alkyl containing up to 6 carbon atoms substituted with 1 to 3 substituents comprising pyridyl or pyridyl substituted at any position with chlorine, bromine, iodine or methyl.

3. A compound in accordance with the claim 1 of the following formula:

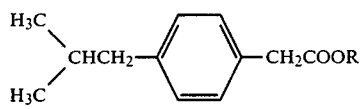

wherein, R is selected from the group consisting of lower alkyl containing up to 6 carbon atoms which is substituted with 1 to 3 substituents comprising pyridyl or pyridyl substituted at any position with chlorine, bromine, iodine or methyl.

4. A compound in accordance with claim 1 wherein the pyridyl group of said pyridyl or substituted pyridyl radical is 2-pyridyl, 3-pyridyl or 4-pyridyl, and wherein said lower alkyl is substituted with only one of said substituents.

5. A method of treating inflammation comprising administering topically an anti-inflammatory amount of a compound in accordance with claim 1.

6. A method of treating inflammation comprising administering topically an anti-inflammatory amount of a compound in accordance with claim 4.

7. A method of treating a patient in need of an analgetic, antipyretic or anti-inflammatory agent comprising orally administering an analgetic, antipyretic or anti-inflammatory amount of a compound in accordance with claim 1.

8. A method for teating a patient in need of an analgetic, antipyretic or anti-inflammatory agent comprising orally administering an analgetic, antipyretic or anti-inflammatory amount of a compound in accordance with claim 4.

9. A method of alleviating symptoms of inflammation comprising orally or topically administering to an animal suffering such symptoms an anti-inflammatory amount of the compound of claim 1.

10. A method of alleviating the symptoms of pain which comprises orally administering to an animal suffering such symptoms an analgetic amount of the compound of claim 1.

11. A method of alleviating the symptoms of fever which comprises orally administering to an animal suffering such symptoms an antipyretic amount of the compound in accordance with claim 1.

* * * * *